United States Patent [19]

Jackson

[11] 4,160,448
[45] Jul. 10, 1979

[54] BLOOD PRESSURE MEASURING CATHETER

[76] Inventor: Richard R. Jackson, Eight Trinity Rd., Marblehead, Mass. 01947

[21] Appl. No.: 799,432

[22] Filed: May 23, 1977

[51] Int. Cl.² .............................................. A61B 5/02
[52] U.S. Cl. ................................................... 128/673
[58] Field of Search ............ 128/2 S, 2.05 D, 2.05 E, 128/2.05 R

[56] References Cited

U.S. PATENT DOCUMENTS

| 3,648,687 | 3/1972 | Ramsey | 128/2.05 D |
| 3,662,743 | 5/1972 | Amarante et al. | 128/2.05 E |
| 3,958,562 | 5/1976 | Hakim et al. | 128/2.05 E |
| 4,050,449 | 9/1977 | Castellana et al. | 128/2 S |

Primary Examiner—William E. Kamm

[57] ABSTRACT

For determining blood pressure a cannula, insertable through a needle into the bloodstream, locates a flaccid, relaxed wall directly in the bloodstream. The relaxed nature of this wall allows direct transmission of the blood pressure to a neutral liquid in the cannula. The cannula transmits this liquid pressure out of the blood vessel to the remote pressure responsive indicator. Thus blood pressure can be directly measured without need of administering anticoagulants to maintain pressure-transmitting conditions.

6 Claims, 8 Drawing Figures

BLOOD PRESSURE MEASURING CATHETER

This invention relates to an improved method of recording blood pressure in a blood vessel such as an artery or vein. Ordinarily for this purpose a plastic needle or cannula is placed in the blood vessel and is either periodically or slowly continually flushed with an anticoagulant solution. The cannula transmits blood to a strain gauge external of the patient. This strain gauge is electrically coupled with a display device showing the blood pressure in the cannula. The mentioned periodic flushing is for the purpose of preventing the blood at the tip of the cannula from clotting and requires the attention of skilled personnel and is disruptive of the procedure. Flush devices have been provided to accomplish this flushing procedure automatically, but are cumbersome and expensive owing to the need for an additional separate liquid flushing cannula for each pressure-measuring site.

My invention comprises a cannula for insertion into the vessel, carrying a small flacid balloon or other form of relaxed membrane exposed on one side to the blood of the vessel and on the other side to saline or other static, neutral liquid which communicates through a liquid-filled cannula to an external transducer sensitive to blood pressure. The relaxed membrane will transmit pressure pulses from the blood to the statically confined neutral liquid without backflow of blood into the cannula, thereby eliminating flush devices, or the necessity of flushing procedures.

In prior blood pressure devices an elastically stretched balloon has been provided on a cannula inserted into the patient's bloodstream for other purposes. When inflated it serves to drag the cannula through the blood vessel, along with the flow of blood, or to temporarily block a blood vessel. In those instances the balloon ordinarily requires continual external fluid pressure for distension. Critical to the quite different use of the present invention is the fact that the wall material of the balloon or membrane is supple, flacid, relaxed, when used, so that it serves as a pressure transmitting membrane from the blood to the neutral pressure-transmitting fluid, and does not permit pressure difference to exist on the opposite sides of the wall.

In one preferred embodiment of the invention an air-permeable membrane is employed, and the fluid volume defined by the system is restricted to an air volume tolerable to the blood-stream. Admission of the neutral pressure-transmitting liquid to this volume causes any air in this volume to be forced through the air-permeable material into the bloodstream, thus assuring that the liquid fills the volume and provides liquid continuity for reliable transmission of the blood pressure. In another embodiment a small air-vent cannula is provided, opening in the volume adjacent the membrane for venting the air outwardly when the neutral liquid is introduced.

These and other objects and features will be understood from the following description taken in conjunction with the figures wherein:

FIG. 1 is a diagrammatic view illustrating a preferred embodiment for positioning a flacid balloon in a blood vessel;

FIGS. 2, 3, and 4, are diagrammatic views respectively of the device prior to insertion, after insertion and inflation, and after evacuation for extraction;

Referring to FIGS. 1–4, the invention comprises a pressure-transmitting catheter 10 having a bore sufficient to transmit blood pressure through liquid that fills the cannula, the cannula carrying at its distal end a balloon 12, and connected at its proximal end to a blood-pressure sensitive strain gauge 14. The fill port 16 is provided for admitting the neutral pressure transmitting liquid. As an example, the cannula may be 36 inches long of 0.065 inch outside diameter and with a bore of 0.30 inches. The balloon 12 is comprised preferably of a hydrophobic air-permeable material such as expanded polytetrafluorethylene open cell foam material marketed under the trademark GORE-TEX by W. L. Gore and Associates Inc. of Newark, Delaware. The balloon wall is, e.g., 0.015 inch thickness, 0.4 g/cc nominal density with pores which transmit air but do not transmit liquid such as water or saline solution. The pores may for instance be of 0.2 micron size.

Figure 1:
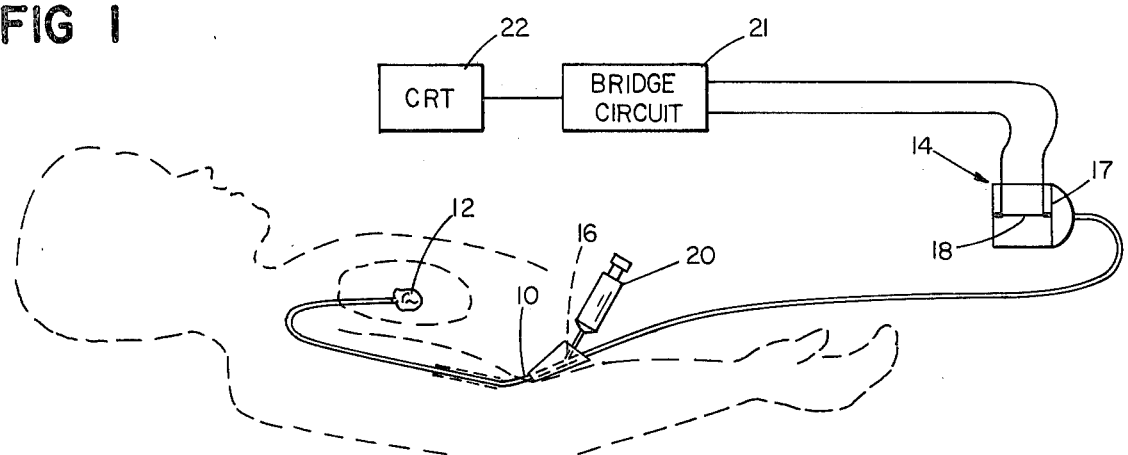
Figure 2:
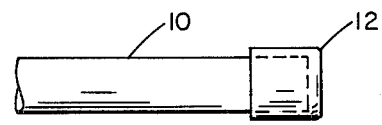
Figure 3:
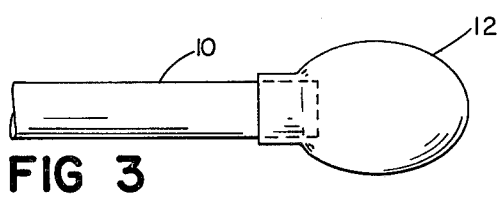
Figure 4:
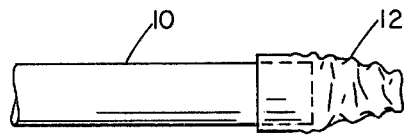
Figure 5:
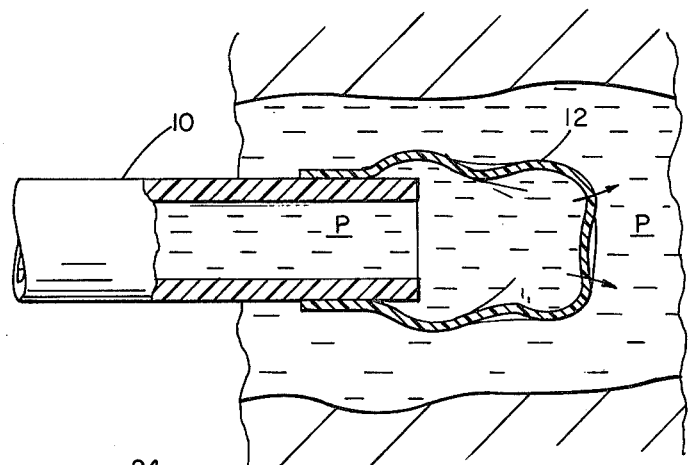
FIG. 5 is a partial view similar to FIG. 1 on an enlarged scale.

This balloon material is secured about the periphery of the end of the catheter 10, and, in the form for introduction into the patient as shown in FIG. 2, lies tightly about the catheter. It is adapted to be inflated and stretched into operative form by the admission of liquid pressure. The intent is to insert the device into the blood vessel, then to admit liquid under pressure to stretch the balloon to the size desired by a predetermined volume of liquid, then to withdraw the liquid to achieve the flacid, relaxed condition critical to the operation of the invention as mentioned above. The procedure is as follows. The cannula is introduced to the blood vessel of the patient in a normal manner, for instance through a large bore needle previously inserted into the blood vessel, or through a so-called "introducer" of known type which is available on the market. The cannula is caused to travel along the blood vessel to the point desired for measurement. After this, syringe 20 is applied to the inlet port 16 and introduces the known quantity of liquid, greater in volume than that of the cannula, the excess being sized to inflate the balloon 12 to the desired dimension. Introduction of the liquid purges the small amount of air in the cannula through the membrane wall, see arrows FIG. 5, into the bloodstream without harmful consequence. In the process of the inflation of the balloon 12, the material permanently yields and thins down, assuming the permanent configuration of a floppy or flacid balloon or cuff, it being understood that the material of this cuff has only limited elastic memory, hence does not return to its original size, but assumes a permanent set condition of greater volume. The syringe is then actuated in the opposite direction to withdraw a known amount of fluid, relieving any stress from the wall of the cuff. Then port 16 is sealed. With the sealing of port 16 a permanent closed system is defined between the balloon and the strain gauge, and with the cuff unstressed, the pressure P in the blood vessel is transmitted to the floppy or flacid non-stressed wall of the cuff 12 to the interior of the balloon as shown in FIG. 5. Hence the same pressure, i.e., the blood pressure within the blood vessel, exists within the balloon in the neutral fluid which fills it, as well as in the blood vessel. This neutral liquid is in a closed, static system, and its pressure is transmitted back through the cannula to the strain gauge transducer 14 which reads blood pressure. As illustrated in FIG. 1, this transducer includes a membrane 16 deflectable under the influence of such pressure, to change the stress upon strain gauge 18. The changed resistance of the strain gauge element 18 is sensed by a Wheatstone bridge circuit 20, and the changes are displayed in cathode ray tube 22. Thus the display on cathode ray tube 22 follows accurately the changes in the blood pressure as sensed by the balloon. When it is desired to terminate blood pressure monitoring and remove the catheter, the syringe 20 is again connected through connection 16, and is actuated to withdraw liquid from the cannula, this having the result of collapsing the balloon 12 upon the end of the cannula as illustrated in FIG. 4. Thereupon the cannula is withdrawn from the blood vessel.

Figure 6:
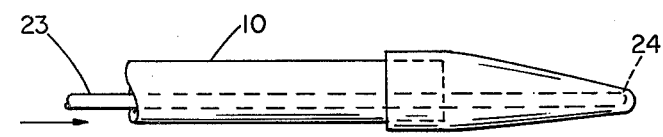
FIG. 6 is a view similar to FIG. 2 of another preferred embodiment, in condition for insertion into a blood vessel.
Figure 7:
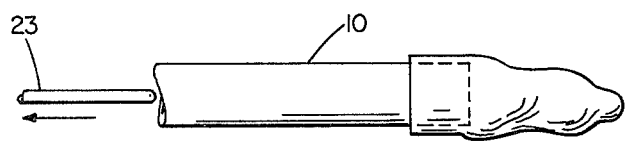
FIG. 7 is a view of the embodiment of FIG. 6 in condition for use.

Referring to FIG. 6, in an alternative construction, the cuff is formed of latex or silicone rubber compound, for instance 0.001 inch wall thickness. For insertion, it is stretched by means of an outwardly protruding stylet 22 which passes through the cannula 10, its tip 24 stretching the balloon into a thin configuration suitable for introduction into the blood vessel. Upon retraction of the stylet, the stretching tension on the cuff is relaxed, and the cuff assumes a floppy, relaxed configuration as shown in FIG. 7. Liquid is introduced in a quantity so limited as to preserve the floppy nonstressed condition of the cuff and measuring the blood pressure proceeds as described in the prior embodiment.

Figure 8:
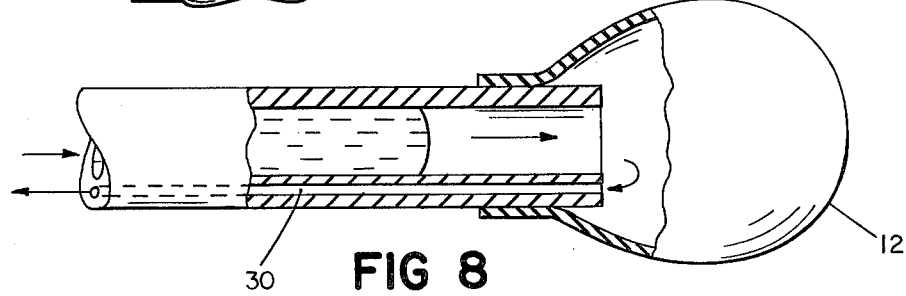
FIG. 8 is a view of another embodiment employing an air-vent catheter.

Referring to FIG. 8, in this embodiment a small size vent cannula 30 is provided to vent air from adjacent the membrane 12 during introduction of the liquid.

What is claimed is:

1. A catheter sized for insertion through a needle-like probe into a blood vessel for the purpose of determining blood pressure, the portion of said catheter insertable through said needle-like probe having a liquid-impermeable, flaccid wall positioned to enter directly into the bloodstream and a cannula communicating from the exterior side of said flaccid wall to a blood pressure-responsive indicator, means for admitting liquid to said cannula to establish a static isolated liquid volume from the flaccid wall to said indicator, said flaccid wall arranged to deflect while in said bloodstream in direct response to the pressure of the blood in the manner to transmit said blood pressure directly to the said isolated static liquid within said cannula and said cannula adapted to transmit the pressure of said isolated liquid out of said blood vessel to said pressure-responsive indicator whereby blood pressure can be determined directly.

2. The catheter of claim 1 wherein said wall is comprised of air-permeable substance.

3. The catheter of claim 1 wherein said wall is in the form of a closed volume communicating with said cannula, defining a balloon sized to lie directly within the blood vessel.

4. The catheter of claim 3 wherein said balloon, in its condition prior to introduction to the patient, is of lesser dimension than operable dimension, said wall being defined by substance susceptible to nonelastic deformation by the application of fluid pressure, adapted to be inflated to said operable dimension by a fixed volume of liquid after placement in the blood vessel of the patient.

5. The catheter of claim 1 wherein said wall is defined by an elastomeric cuff member, and a stylet disposed within said cannula, for stretching said cuff member to a reduced cross-sectional dimension for insertion into said blood vessel, said stylet being adapted to be removed to relax the cuff of said wall of said balloon thereby to enable operation in unstretched, relaxed condition, with the pressure of the blood vessel transmitted through the barrier provided by said cuff to liquid in said cuff.

6. The catheter of claim 1 including means to purge air from said volume during filling with liquid.

* * * * *